United States Patent [19]

Silverstein et al.

[11] Patent Number: 5,025,778

[45] Date of Patent: Jun. 25, 1991

[54] ENDOSCOPE WITH POTENTIAL CHANNELS AND METHOD OF USING THE SAME

[75] Inventors: Fred E. Silverstein, Seattle; Eric A. Opie, deceased, late of Brier, Wash., by Elizabeth Jeanne Opie Salamonsen, executrix

[73] Assignee: Opielab, Inc., Seattle, Wash.

[21] Appl. No.: 498,611

[22] Filed: Mar. 26, 1990

[51] Int. Cl.$^5$ ................................................ A61B 1/00
[52] U.S. Cl. ...................................................... 128/4
[58] Field of Search ............................ 128/3, 4, 5, 6, 7

[56] References Cited

U.S. PATENT DOCUMENTS

| | | | |
|---|---|---|---|
| 2,548,602 | 4/1951 | Greenburg | 128/4 |
| 4,141,364 | 2/1979 | Schultze | 128/4 X |
| 4,592,341 | 6/1986 | Omagari et al. | 128/4 |
| 4,593,699 | 6/1986 | Poncy et al. | 128/660 |
| 4,721,097 | 1/1988 | D'Amelio | 128/4 |
| 4,742,829 | 5/1988 | Law et al. | 128/660 |
| 4,763,662 | 8/1988 | Yokoi | 128/660 |
| 4,784,158 | 11/1988 | Okimoto | 128/771 |
| 4,800,870 | 1/1989 | Reid | 128/6 |
| 4,807,593 | 2/1989 | Ito | 128/4 |
| 4,815,470 | 3/1989 | Curtis et al. | 128/660 X |
| 4,854,302 | 8/1989 | Allred, III | 128/6 |
| 4,928,669 | 5/1990 | Sullivan | 128/4 |
| 4,947,827 | 8/1990 | Opie et al. | 128/4 |

Primary Examiner—William H. Grieb
Attorney, Agent, or Firm—Seed and Berry

[57] ABSTRACT

An apparatus and method for providing an endoscope with a plurality of potential channels is disclosed. A tubing having a radially flexible wall is positioned adjacent the endoscope insertion tube. The tubing is collapsed prior to inserting the insertion tube into the patient's body. After the insertion tube is within the patient's body, the tubing is expanded to create a channel. A medical apparatus may pass through the channel for performing a medical procedure. The tubing is expanded by placing a tapered rod therethrough, by placing a fluid under pressure within the tubing, or by elevating a flat coiled wire into a cylindrical coil. A radially rigid tubing is placed within the expanded flexible tubing to permit medical devices to extend from a position outside of the patient's body to the distal end of the insertion tube. A plurality of tubings are provided circumferentially spaced from each other around the insertion tube to permit a combination of medical devices to be used in cooperation with each other to perform a medical procedure. A stiffening member, such as a rod or fluid under pressure may extend partially along the length of the insertion tube to vary the flexibility characteristics of the insertion tube while it is within the patient's body.

28 Claims, 7 Drawing Sheets

ENDOSCOPE WITH POTENTIAL CHANNELS AND METHOD OF USING THE SAME

DESCRIPTION

1. Technical Field

This invention relates to endoscopes, and more particularly, to a structure and method for providing a channel within the insertion tube of an endoscope.

2. Background of the Invention

Endoscopes are presently used for diagnostic and therapeutic purposes. There are many different uses for endoscopes, and frequently the endoscope design is varied, depending on its use, to optimize the performance of the endoscope for its intended purpose. For example, there are upper endoscopes for examination of the esophagus, stomach and duodenum, urethroscopes for examining the urethra and bladder, colonoscopes for examining the colon, angioscopes for examining the blood vessels and heart, bronchoscopes for examining the bronchi, laparoscopes for examining the peritoneal cavity, arthroscopes for examining joint spaces, and sigmoidoscopes for examining the rectum and sigmoid colon.

Endoscopes must be very flexible to permit the tip of the insertion tube to travel from the point of insertion into the human body to a desired location within the body. The entire endoscope insertion tube must be sufficiently flexible to follow the body cavity as the tip progresses toward the desired location. The tip of the endoscope must also be steerable to permit the physician to place the tip at a selected point for examination, treatment, biopsy or the like. The endoscope may include one or more diagnostic or treatment devices, such as tubings for water, air and biopsy suction; a viewing device, a temperature sensor, a heating probe, an ultrasonic sensor, a laser catheter or the like. The tubings inside the endoscope must be capable of bending or flexing without kinking or collapsing as the endoscope is moved through the body.

Endoscopes must be adequately cleaned and sterilized between each use to ensure that disease is not transmitted from one patient to another. For example, upper endoscopes, colonoscopes, angioscopes and sigmoidoscopes all come in contact with the blood and other body fluids which are capable of transmitting diseases from one person to another. Even though the endoscopes are cleaned between each use, often using chemicals, such as glutaraldehyde, complete sterilization is not ensured. Some body particles may lodge in a crevice of the endoscope and not be contacted by the sterilization fluid.

According to U.S. Pat. No. 4,646,722 to Silverstein et al., incorporated herein by reference, sterilization of the endoscope for each use is ensured by placing a sheath over the endoscope insertion tube prior to use on each patient. In addition, the various tubings which come in contact with body fluids are disposed of and replaced in-between each use.

Presently, a limiting constraint in designing endoscopes is that the diameter of the endoscope must be less than the diameter of the body cavity through which the endoscope must travel. And the ability of a patient to tolerate an endoscope is related to its diameter. An endoscope for use in the stomach cannot be larger in diameter than the esophagus. Endoscopes for use in the gastrointestinal tract cannot be larger in diameter than the rectum, colon or large intestine, depending upon the length which the endoscope is inserted into the digestive tract. Angioscopes for examining the blood vessels and heart must be smaller in diameter than the smallest blood vessel through which the angioscope must pass.

The medical diagnostic and treatment which can be performed using an endoscope may be limited by its diameter. For example, the diameter of the endoscope may not be sufficiently large to permit both an ultrasonic probe and a video probe to be located within the same endoscope. Similarly, the physician may desire to have an endoscope which includes a video probe, a biopsy channel and graspers for removing tissue viewed by the video probe. However, the diameter of the endoscope may be limited to a size smaller than that required to include a grasper, a biopsy channel and a video probe in the same endoscope. The physician may wish to have a temperature sensor, heater probe, multiple-arm grasper, wash channel, forward viewing video probe, side viewing video probe, binocular lens, wide angle lens, ultrasonic sensors, ultrasonic heating devices, lasers, micrometers or the like for use alone or in combination with each other in diagnosing or treating a patient. Unfortunately, the diameter of the body cavity through which the endoscope must pass may not be sufficiently large to permit an endoscope to be routinely passed which is sufficiently large to accomodate more than one or two of the possible diagnostic and treatment devices which might need to be used.

SUMMARY OF THE INVENTION

It is therefore an object of this invention to provide a method of increasing the cross-sectional area of a channel of an insertion tube while the insertion tube is within the patient's body.

It is an object of this invention to provide a tubing having a radially flexible wall coupled to said insertion tube, the tubing having a variable cross-sectional area.

It is another object of this invention to provide a potential channel in an endoscope insertion tube.

It is another object of this invention to provide a device for selectively stiffening a portion of the insertion tube while it is being inserted into the body or after it has been inserted into the body.

These and other objects of the invention as will be apparent herein are accomplished by providing a tubing having a radially flexible wall coupled to an insertion tube of an endoscope. The tubing is sufficiently flexible to be totally collapsed so that its cross-sectional area is approximately that of the wall of the tubing. The channel of the tubing is radially expandable to provide a lumen sufficiently large for matter to pass therethrough. The channel extends along an insertion tube into the body to permit medical devices to pass therethrough and to the body. A plurality of such flexible tubings, each having a respective channel, may be positioned around the outer circumference of the insertion tube.

Numerous methods or devices may be used to expand the tubing. A rigid (but flexible) rod may be insertable into the channel to expand the tubing. A noncollapsible tubing may be carried by the rod into the flexible tubing and remain in the flexible tubing to prevent it from collapsing after the rod is removed. Any selected medical device may then be passed through the tubing to the tip of the endoscope for medical uses. In one embodiment, a plurality of flexible tubings are provided around the insertion tube to permit a plurality of medical devices to extend through the tubings simultaneously for use in a cooperative relationship. Alternatively, the flexible tubing may be expanded by forcing fluid under pressure into the tubing. The bending characteristics of the insertion tube may be changed by inserting a rod into the tubing a selected length. Alternatively, the bending characteristics of the insertion tube may be varied by pumping a fluid under a selected pressure into the tubing over a selected length or portion of the insertion tube. This can be the entire length. The proximal portion (close to the examiner) or another portion of the insertion tube closer to the tip may be selectively stiffened without stiffening either the proximal or distal tip.

DETAILED DESCRIPTION OF THE INVENTION

Figures 1, 2A, 2B:
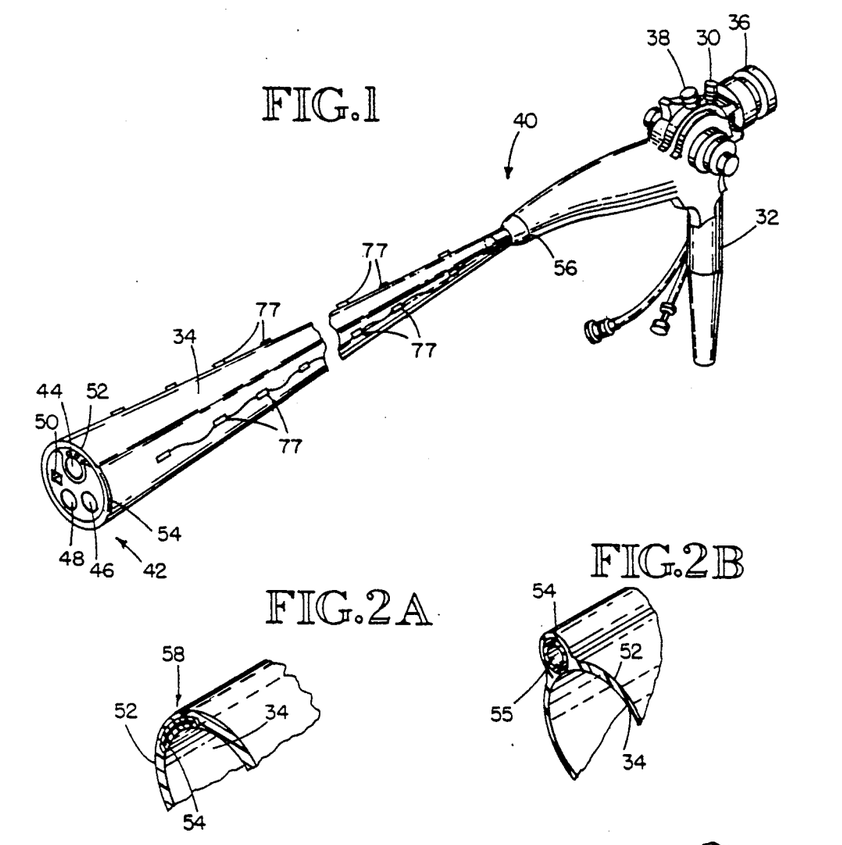
FIG. 1 is an isometric view of an endoscope and insertion tube having a sheath and flexible tubing coupled to the insertion tube.
FIG. 2a is an enlarged isometric view of the flexible tubing in the collapsed state positioned between the sheath and the insertion tube.
FIG. 2b is an isometric view of the flexible tubing of FIG. 2a with the tubing expanded.

An endoscope 30 includes a handle 32 and an insertion tube 34. The handle 32 includes controls 36 for steering and bending the insertion tube 34 as it advances through the human body and while being used to perform a medical procedure. The handle 32 may also include optical viewing ports, sensor readouts, medical treatment devices or the like, labeled generally as 38.

The insertion tube 34 has a proximal end 40 adjacent the handle 32 and a distal end 42. The insertion tube 34 includes a plurality of components, as is well known in the art. For example, the insertion tube may include a biopsy channel 44, an optical viewing device 46, an ultrasonic probe 48 or other medical device 50. The biopsy channel 44 is a disposable tubing resting, in a channel, similar to that described in Serial No. 07/292,473, filed Dec. 30, 1988 by Opie et al. now U.S. Pat. No. 4,947,827 granted Aug. 14, 1990 and incorporated herein by reference, or of the type shown in U.S. Pat. No. 4,646,722. The optical device 46 is a fiberoptic cable, a CCD imager (a TV camera viewing lens) or other optical device as known in the art.

The endoscope 34 is enclosed within a sheath 52. The sheath 52 extends from the distal end 42 to the proximal end 40. The sheath 52 includes a viewing window over the optical device 46 and an appropriate end cap to permit use of medical devices 48 and 50. In the preferred embodiment, the biopsy channel 44 and associated channels which come in contact with body fluids are positioned in a groove of the insertion tube of 42 for easy removal and replacement between patients. The biopsy channel 44 is coupled to the sheath 52 for easy removal, for replacement and for ensuring a complete seal around the insertion tube 34 for sterilization.

A tubing 54 having radially flexible Walls 53 is positioned adjacent the insertion tube 34. The flexible tubing 54 extends from the proximal end 40 to the distal end 42. The flexible tubing 54 includes a channel 55 having a proximal end opening 56 and a distal end 58. The wall of the tubing 54 is sufficiently flexible to be completely collapsed so that the total cross-sectioned area of the tubing 54 is approximately that of the Wall only. When expanded, the channel is so much larger than the wall that the total area is approximately that of the channel 55. The flexible wall 53 may be constructed from many materials, including an elastomeric, rubber, or other materials which permits the tubing to be radially flexible. The tubing 54 is expandable, as shown in FIG. 2b, to provide an open channel 55 The tubing 54 is not required to be longitudinally flexible, though some longitudinal flexibility is permissible.

FIGS. 2a and 2b are enlarged views of the flexible tubing 54 adjacent the endoscope 34. The flexible tubing 54 is held against the insertion tube 34 by the sheath 52. The flexible tubing 54 is a thin-walled membrane which does not significantly increase the cross-sectional diameter of the insertion tube 34 when collapsed, having the channel 55 closed, as shown in FIG. 2a. FIG. 2b illustrates the flexible tubing 54 while expanded, having channel 55 open. The sheath 52 is sufficiently flexible to permit the tubing 54 to expand to the desired cross-sectional area.

Figures 3A, 3B:
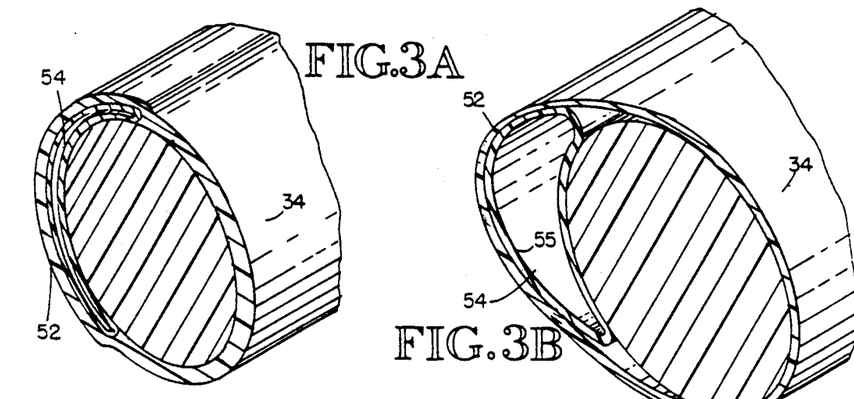
FIG. 3a is an isometric view of a large-radius flexible tubing positioned between the sheath and the insertion tube.
FIG. 3b is an isometric view of the device of FIG. 3a with the flexible tubing expanded.
Figure 4A:
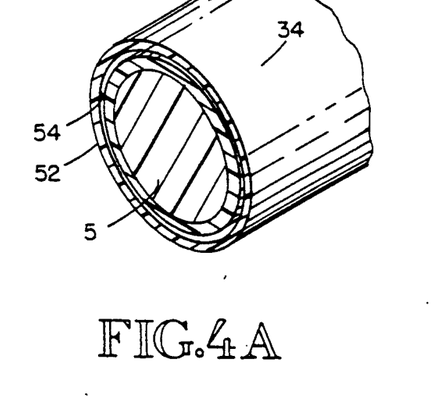
FIG. 4a is an isometric view of a flexible tubing extending circumferentially completely around the insertion tube with the flexible tubing in the collapsed position.
Figure 4B:
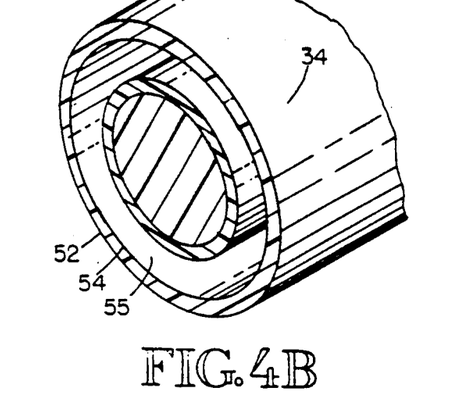
FIG. 4b is an isometric view of FIG. 4a with the flexible tubing in the expanded position.

The tubing 54 may range in size from small, as shown in FIG. 2b, to large, as shown in FIG. 3b, or even larger, as shown in FIGS. 4a and 4b. FIGS. 3a and 3b illustrate a large flexible tubing 54 extending circumferentially around the insertion tube 34. A larger tubing 54 provides a larger channel 55, as shown in FIG. 3b. FIGS. 4a and 4b illustrate a tubing 54 sufficiently large that it extends completely around the insertion tube 34 and is coextensive with the sheath 52. FIG. 4b illustrates the tubing 54 in the expanded state having a channel 55 completely surrounding the insertion tube 34.

Figure 5A:
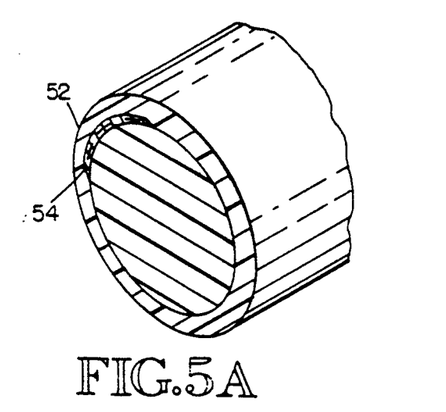
FIG. 5a is an isometric view of a flexible tubing having multiple lumens, each lumen being in the collapsed position.
Figure 5B:
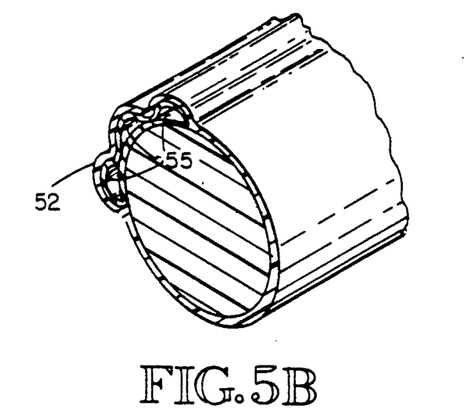
FIG. 5b is an isometric view of FIG. 5a with each lumen of the flexible tubing expanded.

FIGS. 5a and 5b illustrate a tubing 54 having multiple potential channels. A plurality of individual lumens are circumferentially spaced from each other in the tubing 54. Individual channels 55 are formed in the tubing 54 when the respective lumen is expanded. The individual channels 55 are sealed with respect to each other and independently expandable or collapsible. While three lumens are shoWn in the single tubing 54 circumferentially spaced from each other around the insertion tube 34, it will be understood that a greater or fewer number of lumens for forming a desired number of channels 55 in a single tubing 54 can be provided if desired.

Figure 6:
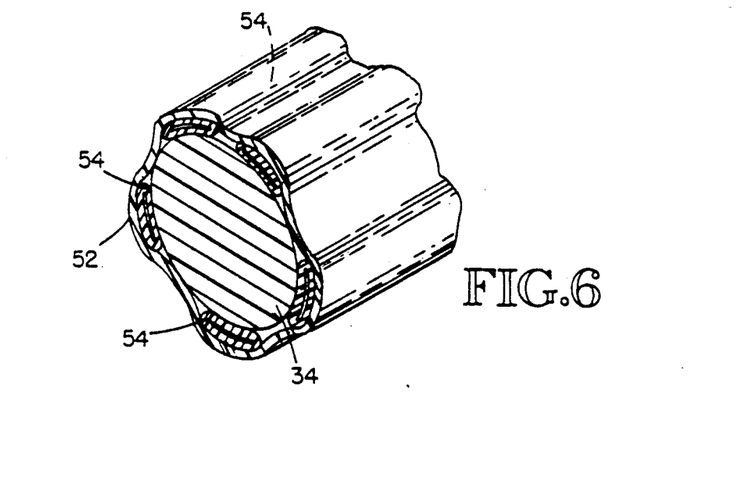
FIG. 6 is an isometric view of an endoscope insertion tube having a plurality of flexible tubings positioned circumferentially around the insertion tube, spaced from each other.

FIG. 6 illustrates a plurality of individual tubings 54 circumferentially spaced with respect to each other around the insertion tube 34. Each tubing 54 has a single lumen forming a potential channel. The lumens of the individual tubings 54 are collapsible and expandable independent of each other to provide channels at desired positions circumferentially around the endoscope 34.

The tubing 52 may be coupled to the insertion tube using many different techniques. In the embodiment of FIGS. 1-8, the tubing 54 is held around the insertion tube 34 by the sheath 52. The tubing 52 abuts against the outer wall of the insertion tube 34 and is held flat against the outer wall by the sheath 52. Because the walls of the tubing 54 are extremely thin compared to the insertion tube 34, the diameter is not significantly larger than that of the insertion tube 34 alone.

Figure 7:
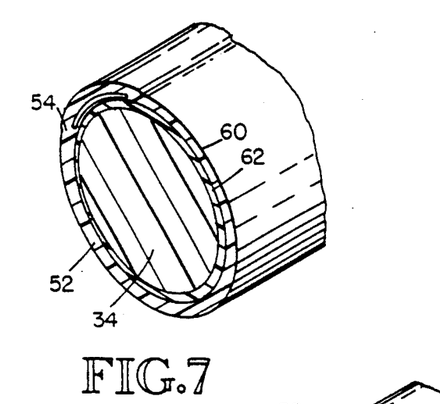
FIG. 7 is an isometric view of a flexible tubing positioned within a wall of the sheath.
Figure 8:
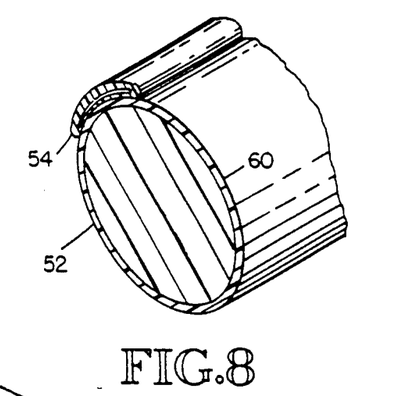
FIG. 8 is an isometric view of a flexible tubing positioned outside the wall of the sheath.
Figure 9:
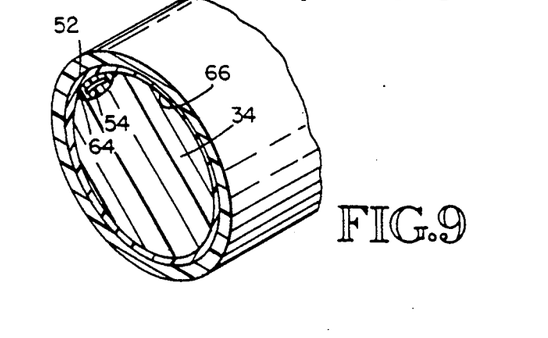
FIG. 9 is an isometric view of an insertion tube having a groove in which the flexible tubing is positioned in the collapsed state.

FIGS. 7-9 illustrate alternative embodiments for retaining the flexible tubing 54 with respect to the insertion tube. FIG. 7 illustrates a flexible tubing 54 which is part of the sheath 52. The lumen to form the channel 55 is within the sheath, being located between an outside wall 60 and an inside Wall 62 of the sheath 52. FIG. 8 illustrates an embodiment in which the tubing 54 is coupled to the insertion tube 34 without a sheath 52. The tubing 54 is held in position on the insertion tube 34 by one of a variety of structures including flexible straps, adhesive between the outer wall 60 of the insertion tube 34 and a bottom surface of the tubing 54 or the like. FIG. 9 illustrates an embodiment in which the tubing 54 is positioned within a recessed groove of the outer wall of the insertion tube 34. Having the tubing 54 positioned in the recessed groove provides an endoscope having a completely smooth sheath 52 surrounding the insertion tube 34. The tubing 54 is generally sufficiently thin that a significant bulge will not occur in the sheath 52 even when no groove is present in the outer wall of the insertion 34; however, in some applications it may be desirable that even a very slight bulge not be present and therefore a groove is provided in the endoscope 34 in which the tubing 54 may be positioned. The groove 64 in the outer wall 66 of the insertion tube may also form as a locating guide for the tubing 54 to ensure that the tubing 54 is positioned at the proper circumferential location with respect to other instruments in the insertion tube 34. The tubing 54 may expand into the groove if desired or force the sheath outward. Tubing having multiple lumens or multiple tubings may also be used in the embodiments of FIGS. 7-9 as illustrated in the embodiments of FIGS. 2a-6.

Figure 10:
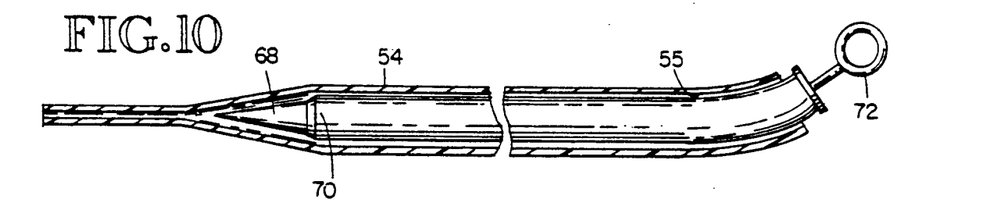
FIG. 10 is a partial, cross-sectional view of an introducer while expanding the flexible tubing.
Figure 11:
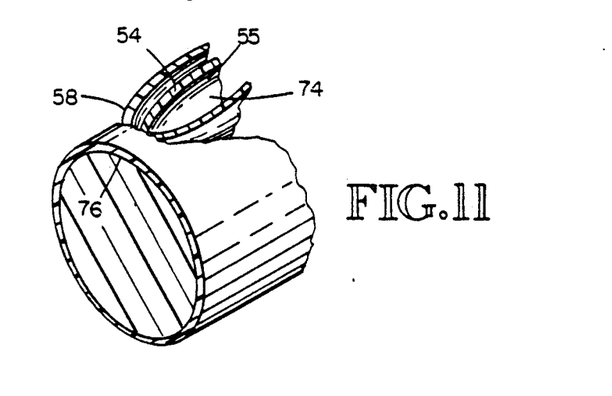
FIG. 11 is an isometric view of the flexible tubing being expanded by fluid under pressure.
Figure 12:
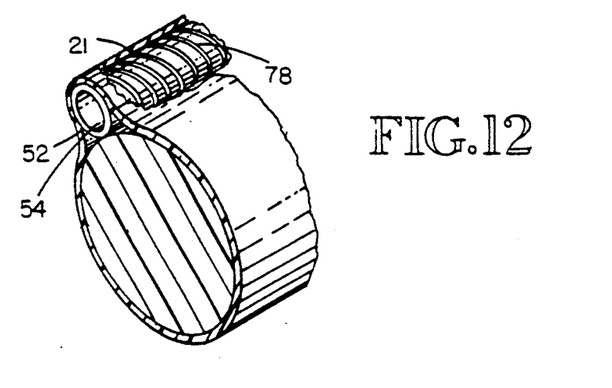
FIG. 12 is an isometric view of the flexible tubing being held in the expanded state by a wire-reinforced tube within said tubing.

FIGS. 10-12 illustrate various devices and methods for expanding the tubing 54 to provide the channel 55. FIG. 10 illustrates a tapered, rigid rod 68 having a radially rigid tubing 70 around the outer surface of the rod 68. The tubing 54 is expanded by forcing the rigid rod 68 through the tubing to smoothly and gradually enlarge the channel 55 by expanding the walls of the tubing 54. After the rod 68 has reached the distal end 58 of the tubing 54, the rod 68 is retracted and the radially rigid tubing 70 remains in the expanded channel 55, holding the channel in the expanded, open position as shown in FIGS. 2b. A wire-reinforced tube 78 as shown in FIG. 12 may be inserted in conjunction with the rod 68 if desired. The rod 68 can be retrieved by pulling on handle 72. Alternatively, the rod 68 may be a collapsible member having a cable or metal pins holding it radially rigid but which collapses when the cable or pins are removed. The rod 68 is either disposed of or sterilized for reuse. Medical devices can then be passed from the proximal end 56 to the distal end 58 of the channel 55 and into the human body.

The rod 68 has a flexible tip to aid in guiding the radially rigid tube 70 into the potential channel and follow the curves of the insertion tube within the human body without damaging the tubing 54. The rod 68 and tubing 70, while being radially rigid are sufficiently flexible in the longitudinal direction to follow the curves and bends of the insertion tube within the human body.

FIG. 11 illustrates an alternative method of expanding the channel 55 by introducing a fluid under pressure into the channel. A Waterjet or air jet is coupled to the proximal end 56 see FIG. 1 and placed in the channel 55 under a desired pressure. The fluid pressure expands the channel 55 to a desired size, the fluid pressure being elected to provide the desired amount of fluid to the distal end 58. An advantage of expanding the tubing 54 with a fluid under pressure is that the amount of expansion is easily and precisely controllable. If only a small amount of fluid is desired, the fluid may be pumped into the tubing 54 under a low pressure to maintain a small cross-sectional profile of the endoscope portion within the human body. The tubing 54 will collapse behind the fluid as it is ejected out of the end of the tubing 54. A nozzle 76 may be provided on the distal end 58 of the tubing 54 to increase the velocity of the fluid as it is expelled from the tubing 54, as may be required for a wash jet, air blast for drying an article or the like. Alternatively, the tubing 54 has no nozzle 76 and merely expels the fluid 74 at the same velocity as it travels along the tubing 52.

FIG. 12 illustrates an alternative embodiment in which the tubing 54 is maintained in the expanded position with a wire-reenforced tube 78. The wire-reenforced tube is introduced by the same method used for the tube 78 as described with respect to FIG. 10. A wire-reenforced tube 78 has the advantages of being relatively strong radially and sufficiently flexible in the longitudinal plane to follow the curves of the human body. The wire-reenforced tubing 78 maintains a channel of a fixed diameter to permit various medical devices to pass therethrough or suction from the human body for removing material from the body.

It is also possible to have a wire reinforcing coil 79 lay flat against the insertion tube inside the potential channel 54. The wire coil 79 is collapsed when the channel is flat. The coil may be repositioned between the flat state and the upstanding, cylindrical shape by retracting an extending cable 21 coupled to the coil while holding the region opposite the cable stationary. When desired, the coil is mechanically repositioned to form a cylinder and keep the channel 54 open.

Use of potential channels provides the significant advantage that a standard endoscope design may be used for many diagnostic procedures With the potential channels being used as required for each specific patient. For one patient, the physician may require use of a heater probe for the medical treatment while another patient requires diagnosis With a biopsy or ultrasonic probe. Unfortunately, the body cavity through which the endoscope must pass is often not sufficiently large to permit an endoscope to be routinely passed which is sufficiently large to allow all of these tools to be simultaneously positioned within the endoscope. The physician is therefore required to buy multiple endoscopes, some having ultrasonic probes, others having video probes, heater probes, suction channels or the like. By positioning potential channels around the insertion tube of an endoscope according to the invention, the diameter of the insertion tube is not significantly increased for insertion into the body cavity. Any one of the potential channels may be selectively enlarged and used for the desired medical procedure. The physician is thus saved the expense of having to buy a large number of endoscopes, each having different medical devices thereon.

Another advantage provided by the use of potential channels is that the comfort to the patient is significantly increased. Some human tissue is somewhat flexible, and has the ability to expand slowly over time when held in a stretched condition. According to the invention, an endoscope insertion tube having a minimum diameter and a plurality of potential channels along an outer diameter is inserted into the body. Because the insertion tube is significantly smaller than would be required if all of the channels were fully expanded to their required diameter during the procedure, the insertion of the endoscope is significantly easier for the physician and more comfortable for the patient. As the body begins to adjust to the endoscope insertion tube being within the body channel, one potential channel is slightly expanded, very slowly if necessary, to provide space to the additional medical procedure at the distal tip. Over time, additional potential channels in respective tubings 54 may be expanded and used for the medical procedure.

In one embodiment, illustrated in FIG. 1, a plurality of tension sensors 77 are positioned along the entire length of the endoscope insertion tube, to determine the stress being placed on the walls of the cavity of the human body through which the endoscope is positioned. The physician is able to monitor the stress on the walls of the cavity over time. As the walls become slightly more flexible or expand, the physician is able to further increase, gradually if necessary, the diameter of the insertion tube as a whole by expanding the potential channels without placing excessive stress on the walls of the human body cavity. The tension sensors 77 also indicate to the phYsician that the body cavity wall is under significant stress at some points, and that further stretching should not be performed. The physician is thus able to ensure that the Wall of the body cavity does not rupture by overstress during the endoscopic procedure. The stress sensors 77 may be any suitable stress sensors, as is known in the art. For example, piezoelectric resistors may be positioned at desired locations along the entire length of the insertion tube, either under the sheath 52 or along the outer surface of the sheath 52. Alternatively, pressure-sensitive resistors, fluid pockets whose pressure increases under outside stress, or other known tension sensors may be used as desired.

A further advantage of the invention is that a universal, "one size fits all" insertion tube may be used for entering different body cavities. The universal insertion tube contains the mechanical structure required for bending and steering the insertion tube and may contain some medical devices. The insertion tube is made as small as reasonably possible to provide the mechanical structure required. The insertion tube 34 is thus significantly smaller than would be required if all desired medical devices were placed within the insertion tube. A sheath 52 having a plurality of potential channels is positioned around the universal insertion tube. The physician then uses only those potential channels which maintain the diameter beloW that of the body cavity under examination without having to purchase individual endoscopes for a particular medical procedure or channel within the body.

Having potential channels located at various positions with respect to the insertion tube permits the endoscope to perform additional functions not previously possible. Current endoscope systems include a small wash jet channel, an air insufflation channel, biopsy channels or suction channels for performing medical treatment. However, in many instances it is useful to have multiple wash channels or a large channel for washing. The potential channel is usable to provide a large quantity of wash water to the distal end of the insertion tube in addition to that which may be provided by the wash jets available in the endoscope. Although the standard endoscope includes a channel for suction, in many instances, an additional channel is required to provide increased suction or for suction at a different quadrant at the tip of the insertion tube. For example, the patient may be suffering from gastrointestinal bleeding and large amounts of blood an clots must be removed quickly. Having potential channels within the insertion tube permits the collapsed potential channels to be opened to large diameter channels with a rigidly stiff tube, such as shown in FIGS. 10 or 12 placed therein to prevent the flexible walls 54 from collapsing under suction. The endoscope is thus provided with increased uses not previously possible with prior endoscope designs.

The invention is coupleable to a conventional endoscope purchased separately. The potential channel 54e may be attached by placing a sheath 52 over the insertion tube 34 or by direct attachment to the insertion tube 34, as shown in FIG. 8. Prior art endoscopes may thus be retrofit with this invention. A further advantage is that the potential channels may be used in an emergency situation during the medical procedure. Not all potential channels are used thereby minimizing the discomfort for the patient and the intrusive nature of the endoscopic procedure. However, should an emergency situation arise requiring additional medical devices at the site of interest, having a plurality of potential channels available for use in addition to the endoscope channels or potential channels being used for the procedure permits the physician to place the required medical devices at the site of interest rapidly without having to remove the endoscope and insert another endoscope in its position.

Figure 13:
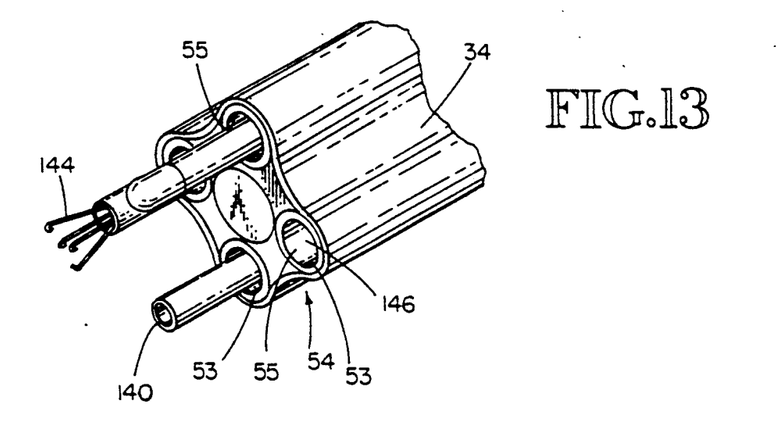
FIG. 13 is an isometric view of a plurality of medical devices extending through a plurality of respective, expanded flexible tubings.
Figure 14:
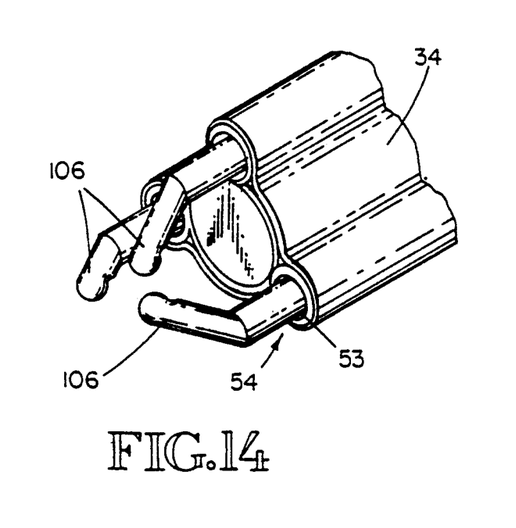
FIG. 14 is an isometric view of a plurality of graspers extending through a plurality of respective, expanded flexible tubings.
Figure 15:
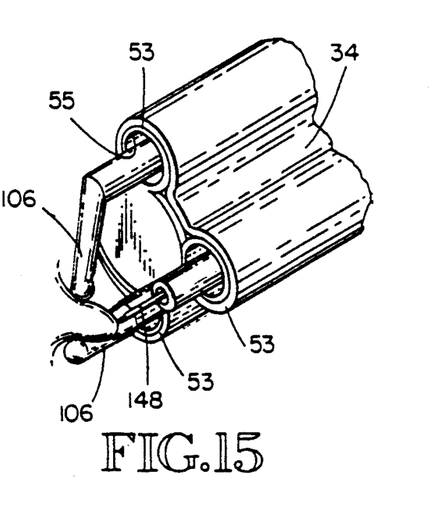
FIG. 15 is an isometric view of a grasper in cooperation with a medical device, each extending respectively through expanded flexible tubings.

Providing a plurality of potential channels in the endoscope permits additional useful accessories to be passed to the endoscope distal end, as shown in FIGS. 13-21. For example, as illustrated in FIG. 13, various wash catheters 142, hemostatic catheters, lasers, heater catheters, graspers, snares, biopsy forceps, suction tubes 146, channels for hydraulic systems to operate, strong grasping catheters 144 or the like, may pass through the potential channels independent of each other and at desired locations as required by the physician. A significant advantage provided by the use of potential channels is that the devices inserted in the potential channels may act in cooperation with each other in a manner not previously possible in the prior art. As illustrated in FIGS. 14 and 15, individual fingers 106 of a strong grasper may extend from respective potential channels. Larger objects may be grasped more firmly than was previously possible in the prior art. The devices extending through each channel may work in cooperation with each other to perform the medical procedure, as illustrated in FIG. 15 in which graspers or fingers 106 hold a part of the human body in a desired position while a device 148 extending through another channel 55 performs a desired medical procedure.

Figures 16, 17:
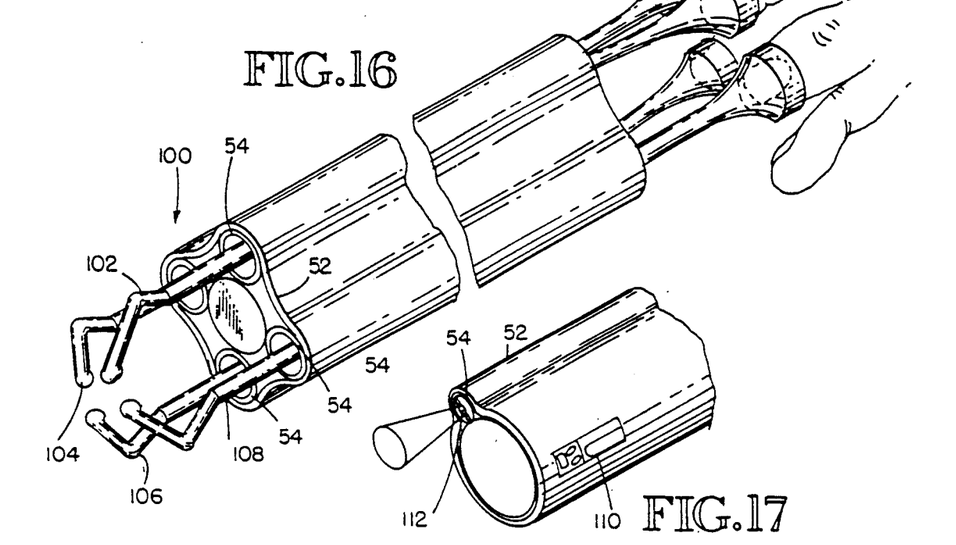
FIG. 16 is an isometric view of a mechanical hand extending through the insertion tube.
FIG. 17 is an isometric view of an end-viewing optical device extending through the expanded flexible tubing in combination With an endoscope having a side-viewing optical device adjacent the tip.

FIG. 16 illustrates a mechanical hand extending along the outer diameter of the endoscope insertion tube for use in a medical procedure. A significant advantage of the use of potential channels is that the individual fingers of the mechanical hand may be positioned in desired quadrants for aid in performing the medical procedure. For example, if the finger 106 of the mechanical hand 100 is not in the proper quadrant to aid in performing the medical procedure, the finger 106 can be removed, thus decreasing the cross-sectional area of the endoscope portion within the human body. If necessary, the finger 106 is inserted through a different potential channel 54 than the previous channel through which it extended to aid in the medical procedure. The overall diameter of the endoscope insertion tube is maintained constant or relatively small even though different channels are used by the fingers because one tubing 54 collapses to decrease the diameter of the endoscope prior to inserting the finger through another tubing 54.

Figure 18:
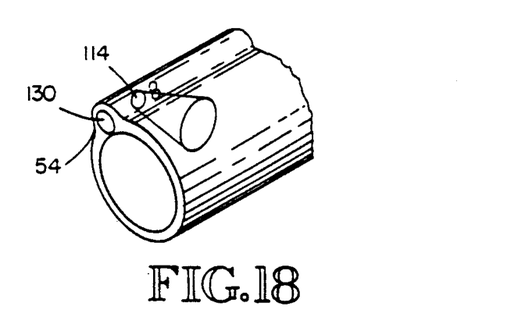
FIG. 18 is an isometric view of a side-viewing optical device extending through the expanded flexible tubing.
Figure 19:
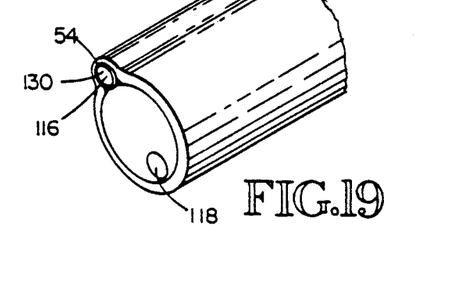
FIG. 19 is an isometric view of an additional optical device extending through the expanded flexible tubing.

The potential channel 54 is usable as an accessory optical channel to increase the optical characteristics of the endoscope. For example, the physician may presently own an endoscope having an outdated optical device, such as a fiberoptic cable at one end thereof. The additional uses are economically provided by coupling a potential channel tubing 52 to an existing endoscope rather than buying an entire new endoscope. By placing a potential channel adjacent the insertion tube of the endoscope, the endoscope is provided with an additional channel which is usable as a CCD imager, small TV camera or other optical viewing device to supplement that presently being used on the endoscope, as illustrated in FIG. 17. Some endoscopes as constructed include side viewing optics 110, as illustrated in FIG. 17. The potential channel may include forward viewing optics 112 to supplement the optics of the endoscope such as by providing binocular viewing or of a different field. Similarly, as illustrated in FIG. 18, an endoscope having no optical devices or a forward looking optical device may be supplemented by a side viewing optical device 114 inserted in potential channel 55 of the tubing 54. FIG. 19 illustrates an additional optical device, such as a wide-angle lens, a magnifying lens, binocular lens or the like positioned in the flexible tubing 54 to supplement the optical device 118 of the endoscope. The optical device 116 may operate in cooperation with the optical device 118 to provide binocular vision if desired. Alternatively, two optical systems can be inserted for binocular vision.

As shown in FIGS. 25a and 25b, the distal end of the potential channel 54 can also be sealed with a clear lens 130 so that the inserted optical device does not get contaminated. The clear lens 130 lays flat, when the tubing 54 is collapsed but stands upright to permit viewing from the end of tubing 54 when the tubing 54 is expanded. The lens may be pulled up mechanically by a wire (not shown) or may be fixed to specific regions of the top and bottom of the tubing 54 to stand it up as the tubing expands.

Figure 20:
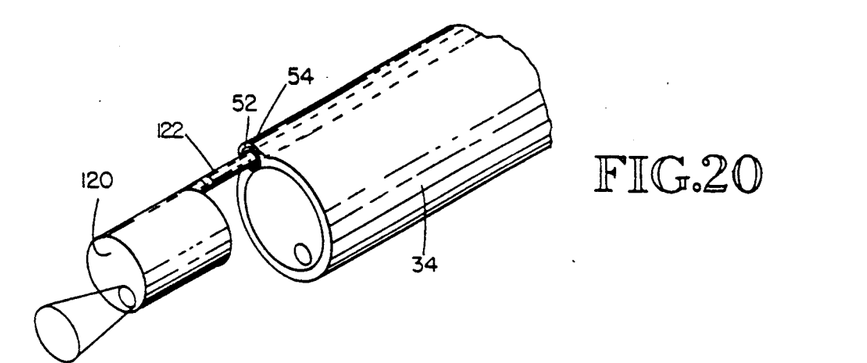
FIG. 20 is an isometric view of a pod control cable extending through the expanded flexible tubing.

FIG. 20 illustrates use of the potential channel to provide control of totally new endoscope functions contained within the functional pod 120 at the end of the endoscope. The pod may include: ultrasonic transducers for imaging, Doppler shift measurements or for hyperthermia; cameras; heating probes; TV systems; microsensors; monofilament quartz members to support a laser coagulating system; hydraulic tubes for activating grasping, suturing or biopsy devices; suction lines to activate biopsy devices; microwave antenna to activate microwave heaters; or the like. An existing endoscope may not have sufficient medical devices coupled thereto but have adequate mechanical features for continued use. A pod may be provided coupled to the distal end of the insertion tube containing the additional medical devices. The mechanical structure of the insertion tube 34 provides the steering and tip control necessary for the medical procedure even though the medical devices contained therein may be inadequate or outdated. A control cable 122 extends through the tubing 54 to the pod 120 to provide control of the medical devices within the pod 120. Significant medical features are thus provided to an endoscope by use of the tubing 54 held adjacent the insertion tube 34 by the sheath 52.

Figure 21:
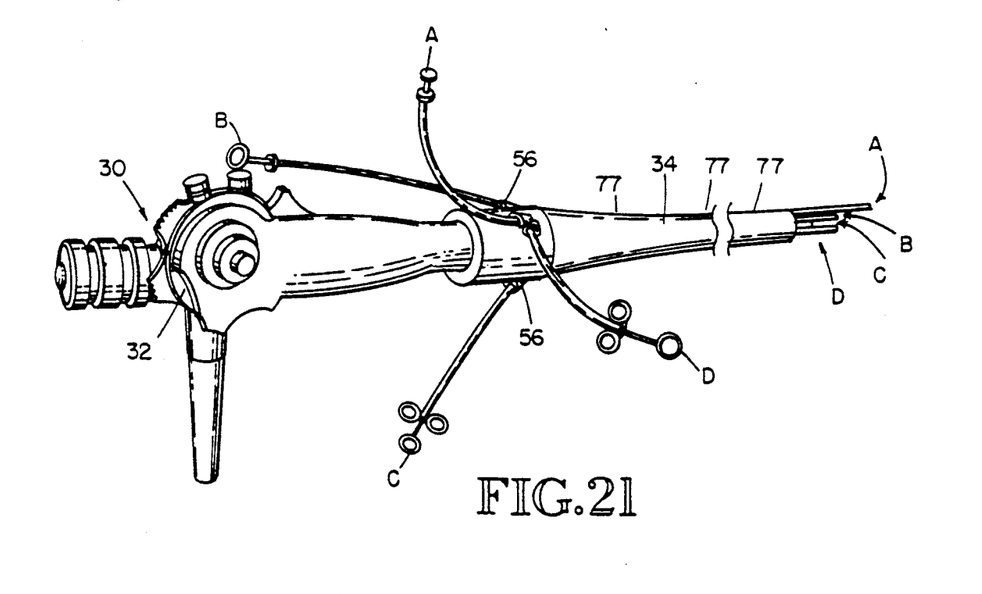
FIG. 21 is an isometric view of an endoscope having a plurality of independently controlled medical devices extending from the proximal end of the insertion tube to the distal end through respective expanded flexible tubings.

FIG. 21 illustrates the case of multiple catheters at the same time via the multiple potential channels around the circumference of the endoscope. The potential channels permit multiple functions to be performed during a complex medical procedure. For example, during hemostatic therapy for control of bleeding, multiple channels may be required for use of suction, extra light, extra wash catheters and the need to pass several hemostatic devices, such as heater probes, electrocoagulation probes or the like to the bleeding site. Operations may be performed inside the intestine, heart, lung or other organ system of the body using the multiple catheters in cooperation with each other during the procedures. The individual catheters are controlled by respective persons assisting the primary endoscopist while the entire procedure is followed on a large screen TV or other optical viewing device. Smooth, easy and effective coordination of the multiple functions during the procedure are provided by the individual persons working together. Individual persons can each control a separate function throughout the medical procedure.

Figures 22A, 22B:
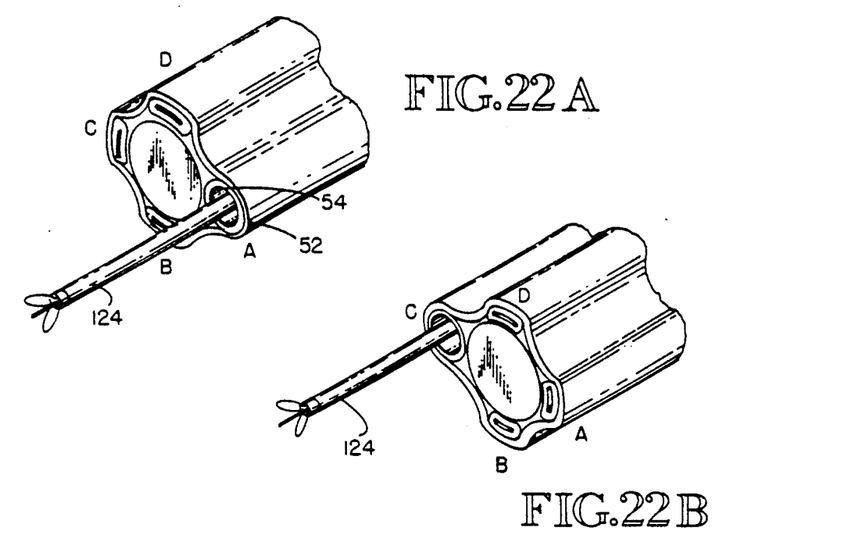
FIG. 22a is an isometric view of a medical device extending through one of a plurality of flexible tubings for positioning in a desired quadrant.
FIG. 22b is an isometric view of the medical device of FIG. 22a extending through a different flexible tubing adjacent the insertion tube for positioning in a different quadrant.

FIGS. 22a and 22b illustrate the advantage of providing multiple potential channels to permit the medical device to be located in the desired quadrant For example, as illustrated in FIG. 22a, the biopsy forceps are advanced in a first potential channel through tubing 54 to remove a sample tissue for testing. With standard endoscopes not having potential channels, significant steering, rotation and deflection of the endoscope is required in order to attain the sample of the required tissue. Sometimes, the tissue to be acquired is in a position which is difficult or impossible to reach using the standard channel provided in the endoscope. The patient experiences significant discomfort while the physician is attempting to acquire a sample. According to the invention, the tissue to be acquired is positively located using the optics of the insertion tube. The biopsy device 124 is then extended through the appropriate tubing 54 to the desired quadrant. If the sample cannot be obtained from one potential channel, the biopsy forceps are withdrawn and extended through the appropriate potential channel, as shown in FIG. 22b. The total diameter of the insertion tube remains small because the forceps are withdrawn from one potential channel prior to being inserted into the other potential channel.

Figures 23, 24:
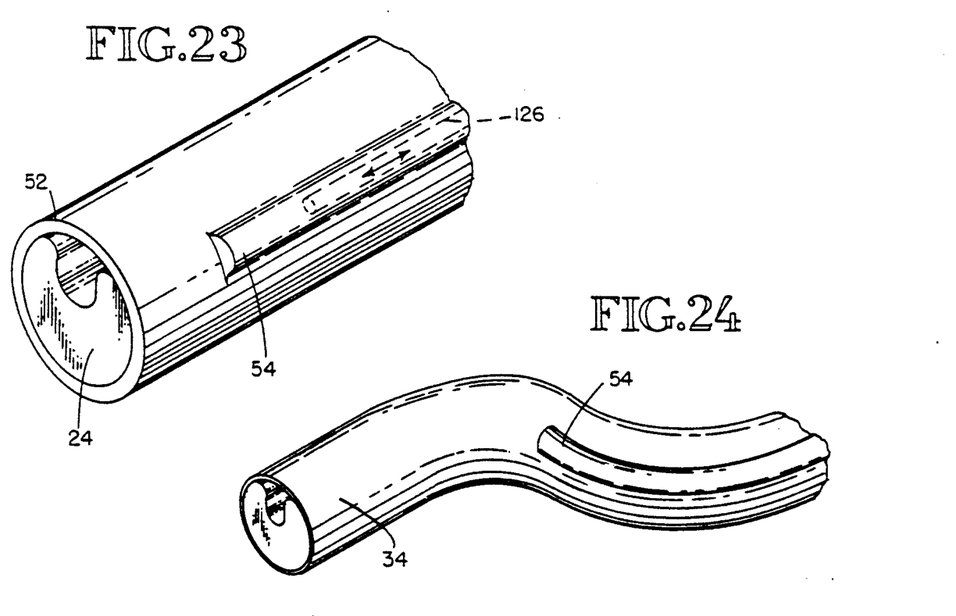
FIG. 23 is an isometric view of a device for varying the bending characteristics of the insertion tube while it is within the human body.
FIG. 24 is a side elevational view of an endoscope having a flexible tubing extending for only part of the length of the insertion tube.

FIGS. 23 and 24 illustrate use of the expandable tubing 54 to vary the flexibility of the insertion tube. In many instances it is desirable or necessary to change the flexibility of an endoscope during a procedure. As the endoscope is inserted into the human body, the tip must be sufficiently stiff, to permit it to be pushed forward from the rear. The insertion tube must not be so flexible as to bend on itself and bunch up when being pushed forward into the body. Once the tip reaches the site for the medical procedure, the medical procedure may require that the tip be extremely flexible and bend through greater than 180° to perform the medical procedure. The flexible tubings 54 provide the ability to control the flexibility of the endoscope during a procedure.

FIG. 23 illustrates a stiff member 126, such as a cable, rod or other device inserted into a tubing 54 to make the insertion tube 34 more rigid. Having the cable, rod or other stiffening member in the tubing 54 prior to the need for bending ensures that the insertion tube will not fold on itself while in a larger cavity. As the insertion tube 34 is advanced into the human body and approaches a sharp bend requiring flexibility, the stiffening member, such as the rod, is retracted from the tubing 54 to permit the insertion tube to bend around the corner. As the increased flexibility of the insertion tube is required, the stiffening member is withdrawn from the tubing 54. The stiffness of the member 126 is selected based on the desired change in flexibility of the insertion tube. If a very stiff insertion tube is desired, the stiffening member 126 is a very rigid rod, but if only a slight change is desired, the member 126 may be cable or flexible rod. The tubing 54 used for varying the bending properties of the insertion tube extends to the end of the tube, opening at the distal end and may be used later for a medical procedure. Alternatively, the tubing may terminate prior to the distal end, as shown in FIG. 24. The stiffening rod 126 may be used anywhere along the insertion tube length, depending on the bending characteristics required.

A colonoscope is one type of endoscope in which the ability to vary the flexibility of the insertion tube is useful. When the tip of the colonoscope is advanced halfway up the cecum, it is helpful if the portion of the insertion tube at the anal verge be relatively rigid and inflexible. The portion beyond the anal verge must be relatively flexible. According to the invention, the entire insertion tube is relatively rigid as it advances through the rectum towards the anal verge. After the insertion tube passes the anal verge, the portion from the anal verge to the body exit at the anus remains relatively rigid with the tip portion beyond the anal verge being flexible. As the insertion tube is advanced through the colon, the stiffening member is gradually retracted to hold the posterior portion of the insertion tube relatively rigid While permitting the portion from which the rod is withdrawn to have the desired bending and steering characteristics.

In an alternative embodiment, as illustrated in FIG. 24, the tubing 54 extends only partially along the length of the insertion tube to provide stiffening of a desired portion of the insertion tube. The potential channel 54 extends approximately three-fourths of the Way along the length of the insertion tube 34. The tubing 54 terminates at the desired location and is fluid tight. Inflating the tubing 54 with fluid 128, such as air or water under pressure, selectively stiffens that portion of the endoscope. In the example of a colonoscope, when the tip has advanced halfway to the cecum the portion at the anal verge is made less flexible by inflation of tubings 54 to selectively stiffen the portion of the insertion tube extending from the proximal end to the anal verge. Using a fluid 128, the change in flexibility can be controlled by many methods, such as by controlling the pressure by the selection of fluid used (whether water, oil, air or other fluid), by the diameter of the tubing 54 and by the number of tubings 54 that are inflated. The endoscope may be selectively stiffened at different portions along its length by providing a small-diameter tubing 54 which expands to a larger-area tubing 54 at selected portions along the length of the endoscope. The insertion tube 34 will be made more stiff by the larger-diameter sections of the tubing 54 than by the smaller-diameter sections though the pressure is the same along the entire length of the tubing.

The apparatus and method of varying the flexibility of the endoscope as shown and described with respect to FIGS. 23 and 24 is usable with conventional endoscopes not having a sheath 52 coupled thereto. Tubings of varying diameter, length and number are attachable on the outside of the insertion tube, inside the insertion tube or at desired locations. Inflating the channels with a fluid or stiffening by inserting a solid rod therethrough dramatically alters the flexibility of the insertion tube of the endoscope. The same techniques used to vary the flexibility of an insertion tube having a sheath are also usable on insertion tubes without a sheath. The invention is thus useful in many types of endoscopes in addition to those having a sheath around an outer surface.

We claim:

1. An endoscope comprising:
   an insertion tube having a distal end for inserting into a patient's body and a proximal end remaining outside said body;
   a sheath covering said insertion tube, said sheath extending from said distal end of said insertion tube to said proximal end of said insertion tube; and
   a resilient tubing within said sheath having a channel that is collapsed in its relaxed state and expandable to provide a lumen through said tubing.

2. The endoscope according to claim 1 wherein said channel is expandable from generally closed to generally fully 3. The endoscope according to claim 1 wherein said channel is expanded by extending a medical diagnostic or treatment device from said insertion tube proximal end to said insertion tube distal end.

4. The endoscope according to claim 1 wherein said channel is expanded by fluid pressure.

5. The endoscope according to claim further including a second resilient tubing disposed between an outer wall of said sheath and said insertion tube, said second resilient tubing having a channel that is collapsed in its relaxed state against said insertion tube and expandable to provide a lumen through said tubing, said second resilient tubing being circumferentially offset from said first resilient tubing around said insertion tube.

6. The apparatus according to claim 5, further including a first medical diagnostic device extending from said proximal end to said distal end in said first resilient tubing and a second medical device extending from said proximal end to said distal end in said second resilient tubing, said first and second medical devices working in cooperation with each other to perform a medical procedure.

7. The apparatus according to claim 5 wherein said first resilient tubing and said second flexible tubing are formed from a single member extending circumferentially around said insertion tube.

8. The apparatus according to claim 5 wherein said first resilient tubing and said second resilient tubing are individual members spaced from each other circumferentially around said insertion tube.

9. The apparatus according to claim 1, further including an expanding means for forcibly expanding said tubing to increase said tubing cross-sectional area.

10. The apparatus according to claim 9 wherein said expanding means includes a tapered, rigid rod and means for moving said tapered, rigid rod from said proximal end of said insertion tube, through said resilient tubing to a selected location Within said flexible resilient.

11. The apparatus according to claim 10, further including means for removing said tapered, rigid rod and means for maintaining said tubing int he expanded condition after said rod is removed.

12. The apparatus according to claim 1, further including a radially rigid tubing positioned within said resilient tubing for preventing said flexible tubing from collapsing.

13. The apparatus according to claim 12 wherein said radially rigid tubing is inserted into said resilient tubing while said insertion tube is within said patient's body.

14. The apparatus according to claim 1 wherein said resilient tubing extends from said insertion tube proximal end to said insertion tube distal end, said resilient tubing having an opening at said distal end to permit material to pass from said resilient tubing to said body or from said body to said resilient tubing.

15. The apparatus according to claim 1, further including a grasping means extending from said proximal end to a position external to said distal end for manipulating material within said body.

16. The apparatus according to claim 1 wherein said tubing extends from said insertion tube proximal end and terminates prior to said insertion tube distal end.

17. The apparatus according to claim 1, further including a means for inserting into said resilient tubing to increase the resistance to bending of said insertion tube.

18. The apparatus according to claim 1, further including a coil within said resilient tubing which lays flat when said channel is collapsed and which stands upright in a cylindrical form to cause said channel to expand.

19. The apparatus according to claim 1 wherein the end of said tubing is sealed to prevent matter from passing from outside said tubing to inside said tubing.

20. The apparatus according to claim 1 wherein the center of expansion for said resilient tubing is radially offset from a longitudinal center of said insertion tube.

21. The apparatus according to claim 1 wherein a portion of said resilient tubing expands outward and a portion remains relatively fixed against said insertion tube when said tubing is expanded.

22. An endoscope comprising:
   an insertion tube having a distal end for inserting into a patient's body and a proximal end remaining outside said body;
   a sheath covering said insertion tube, said sheath extending from said distal end of said insertion tube to said proximal end of said insertion tube; and
   a tubing coupled to said sheath and having a channel and a flexible wall surrounding said channel, said wall being sufficiently flexible to permit varying of the cross-sectional area of said tubing from having generally the cross-sectional area of said wall to having generally the cross-sectional area of said channel.

23. The endoscope of claim 22 wherein said tubing extends from said distal end to said proximal end and said channel opens into said body at said distal end for inserting a medical device into said body through said tubing.

24. The method of providing a channel in an insertion tube of an endoscope, comprising:
   placing a thin-walled, flexible sheath over said insertion tube;
   positioning a tubing having a radially flexible wall adjacent said sheath;
   positioning said insertion tube within a patient's body; and
   expanding a channel in said tubing to a lumen through which material may pass.

25. The method according to claim 24 wherein said expanding step includes the steps of:

inserting a rigid member into a proximal end of said tubing;

moving said rigid member from said proximal end toward a distal end of said tubing;

inserting a tubing having a radially rigid wall into said radially flexible tubing; and removing said rigid member from said tubing.

26. The method according to claim 24 Wherein said expanding step includes inserting a fluid under pressure into said flexible tubing.

27. The method according to claim 24, further including the step of inserting a rigid rod into said flexible tubing for modifying the bending characteristics of said insertion tube.

28. The method according to claim 27, further including the steps of:

placing said rigid rod into said tubing for a predetermined length of said insertion tube prior to placing said insertion tube into said patient;

advancing said insertion tube having said rigid rod extending through said flexible tubing into said patient;

removing said rigid rod from a portion of the length of said tubing; and advancing said insertion tube farther into said patient's body.

* * * * *

UNITED STATES PATENT AND TRADEMARK OFFICE
CERTIFICATE OF CORRECTION

PATENT NO. : 5,025,778

DATED : June 25, 1991

INVENTOR(S) : Fred E. Silverstein et al.

It is certified that error appears in the above-identified patent and that said Letters Patent is hereby corrected as shown below:

In column 13, claim 2, line 22, after "fully" please insert -- open. --.

In column 13, claim 5, line 29, after "claim" please insert -- 1, --.

In column 13, claim 10, line 61, please delete "Within" and substitute therefor -- within --.

In column 13, claim 10, line 62, after "resilient" please delete "." and substitute therefor -- tubing. --.

Signed and Sealed this

Twelfth Day of January, 1993

*Attest:*

DOUGLAS B. COMER

*Attesting Officer*   Acting Commissioner of Patents and Trademarks